(12) United States Patent
Brophy

(10) Patent No.: US 11,426,549 B2
(45) Date of Patent: Aug. 30, 2022

(54) MAGNETIC INTUBATION APPARATUS

(71) Applicant: Samuel Langner Brophy, Victoria (CA)

(72) Inventor: Samuel Langner Brophy, Victoria (CA)

(73) Assignee: First Pass Innovation Inc., Victoria (CA)

( * ) Notice: Subject to any disclaimer, the term of this patent is extended or adjusted under 35 U.S.C. 154(b) by 338 days.

(21) Appl. No.: 16/848,735

(22) Filed: Apr. 14, 2020

(65) Prior Publication Data

US 2021/0316097 A1 Oct. 14, 2021

(51) Int. Cl.
*A61M 16/04* (2006.01)
*A61M 16/00* (2006.01)

(52) U.S. Cl.
CPC .... *A61M 16/0488* (2013.01); *A61M 16/0003* (2014.02); *A61M 16/0051* (2013.01); *A61M 2205/18* (2013.01); *A61M 2205/583* (2013.01); *A61M 2205/587* (2013.01)

(58) Field of Classification Search
CPC .................................................. A61M 16/0488
See application file for complete search history.

(56) References Cited

U.S. PATENT DOCUMENTS

2003/0073935 A1* 4/2003 Segawa .................. A61B 5/065
600/593
2017/0304571 A1* 10/2017 Bailey ................ A61B 1/00154

* cited by examiner

*Primary Examiner* — Travis R Hunnings
(74) *Attorney, Agent, or Firm* — Orin Del Vecchio

(57) ABSTRACT

An endotracheal tube insertion apparatus configured to assist in the proper placement of an endotracheal tube during patient intubation. The present invention includes an external member wherein the external member has a housing with an arcuate formed bottom surface configured to be superposed a patient's neck during intubation. The external member includes a proximity sensor and a magnet. The endotracheal tube insertion apparatus further includes an insertion member that is elongated in form and has movably coupled thereto an end member. The end member is positioned so as to extend beyond the end of the endotracheal tube. The end member includes a proximity tag member and a magnet member wherein the magnet member is configured to be attracted to the magnet located in the external member so as to guide the endotracheal tube to the correct location. A plurality of lights further provides visual confirmation of the proper location.

20 Claims, 3 Drawing Sheets

MAGNETIC INTUBATION APPARATUS

FIELD OF THE INVENTION

The present invention relates generally to healthcare apparatus, more specifically but not by way of limitation, an endotracheal intubation apparatus wherein the apparatus of the present invention is configured to ensure proper placement of an endotracheal tube through utilization of magnetic forces and proximity sensing.

BACKGROUND

Millions of endotracheal intubations are performed each year. As is known in the art, endotracheal intubations are required in order to maintain open airways for patients who are unconscious or unable to breathe on their own. Endotracheal intubations are routinely performed prior to surgical procedures or in the event of a trauma. Typically, the procedure is performed utilizing a laryngoscope wherein the user inserts the laryngoscope into the mouth of the patient with the blade of the laryngoscope directed to the patient's right tonsil. Once the blade reaches the right tonsil, the laryngoscope is swept to the patients midline, keeping the tongue on the left to bring the epiglottis into view. The blade of the laryngoscope is then advanced until it reaches the angle between the base of the tongue and the epiglottis. Next, the laryngoscope is lifted upward towards the chest and away from the nose so as to bring the vocal cords into view. Following this step, an endotracheal tube is inserted into the mouth and through the vocal cords to the point where the expandable cuff is slightly posterior the vocal cords and the cuff is then inflated so as to prevent leakage.

One problem encountered in the conventional procedure of endotracheal intubation is determining whether or not the tube has been inserted the correct distance. If the endotracheal tube is inserted past the carina, only the right lung of the patient will be intubated which can cause pneumothorax of the left lung. To avoid the complication of pneumothorax of the left lung the endotracheal tube must not extend posterior of the tracheal bifurcation. Typically in a hospital environment or where access permits, an x-ray of the patient subsequent intubation can be utilized to ensure proper placement of the endotracheal tube if needed. If this confirmation is required, the time involved for x-ray confirmation can potentially result in significant complications if a pneuomothorax of the left lung exists. Additionally, for intubation performed in environments where there is no access to x-ray equipment there is no accurate means of ensuring proper placement of the endotracheal tube. Another issue during the procedure of endotracheal intubation is accidental insertion into the esophagus. The incorrect insertion of an endotracheal tube into the esophagus can cause serious problems such as but not limited to esophageal perforation.

It is intended within the scope of the present invention to an endotracheal tube insertion assistance apparatus that is operable to ensure proper placement utilizing both magnetic attraction and proximity sensing to direct and ensure the correct position of the endotracheal tube.

SUMMARY OF THE INVENTION

It is the object of the present invention to provide an endotracheal tube insertion apparatus that is configured to assist in the proper placement of an endotracheal tube wherein the present invention includes an external member that is configured to be placed over the patient's neck.

Another object of the present invention is to provide an apparatus configured to assist in the proper placement of an endotracheal tube wherein the external member includes a housing having a bottom surface that is arcuate in shape to mateably superpose a human neck.

A further object of the present invention is to provide an endotracheal tube insertion apparatus that is configured to assist in the proper placement of an endotracheal tube wherein the external member includes a magnet.

Still another object of the present invention is to provide an apparatus configured to assist in the proper placement of an endotracheal tube wherein the external member further includes an integrated proximity sensor such as but not limited to a radio frequency sensor.

An additional object of the present invention is to provide an endotracheal tube insertion apparatus that is configured to assist in the proper placement of an endotracheal tube that further includes an insertion member that is configured to be inserted into the hollow passage of an endotracheal tube.

Yet a further object of the present invention is to provide an apparatus configured to assist in the proper placement of an endotracheal tube wherein the insertion member includes an elongated body having a plurality of sections.

Another object of the present invention is to a provide an endotracheal tube insertion apparatus that is configured to assist in the proper placement of an endotracheal tube wherein the body of the insertion member includes an integrated magnet.

An alternate object of the present invention is to provide an apparatus configured to assist in the proper placement of an endotracheal tube wherein the body of the insertion member further includes a ball joint or similar structure operably coupling the end segment and the adjacent segment.

Still a further object of the present invention is to provide an endotracheal tube insertion apparatus that is configured to assist in the proper placement of an endotracheal tube wherein the end segment further includes an integrated radio frequency tag.

An additional object of the present invention is to provide an apparatus configured to assist in the proper placement of an endotracheal tube wherein the body of the insertion member further includes a conical guide member secured thereto.

A further object of the present invention is to provide an endotracheal tube insertion apparatus that is configured to assist in the proper placement of an endotracheal tube wherein the external member further includes indicator lights configured to provide confirmation of proximity detection of the end member of the body of the insertion member.

An alternative objective of the present invention is to provide a endotracheal tube insertion apparatus wherein the magnet in the external member is configured to attract the magnet in the end segment of the body so as to guide in the proper direction for successful endotracheal tube insertion.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
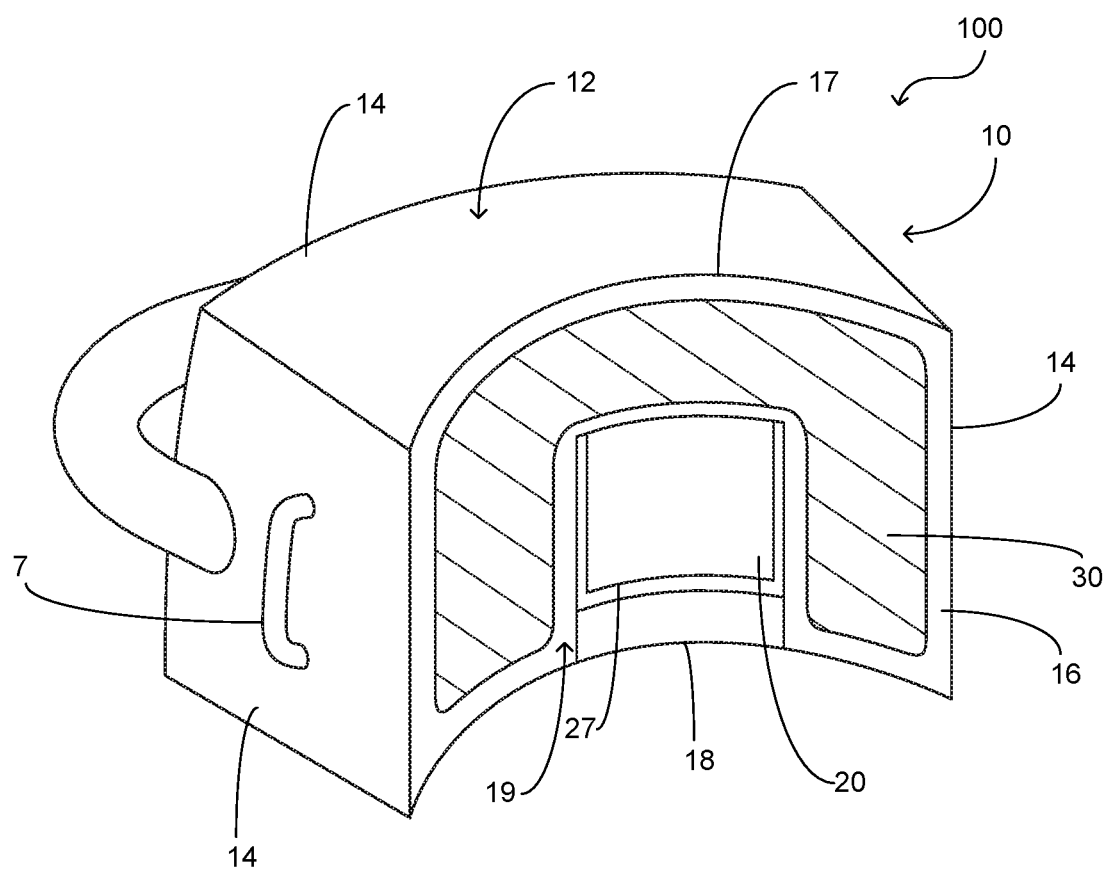
FIG. 1 is a bottom perspective view of the external member of the present invention.
Figure 2:
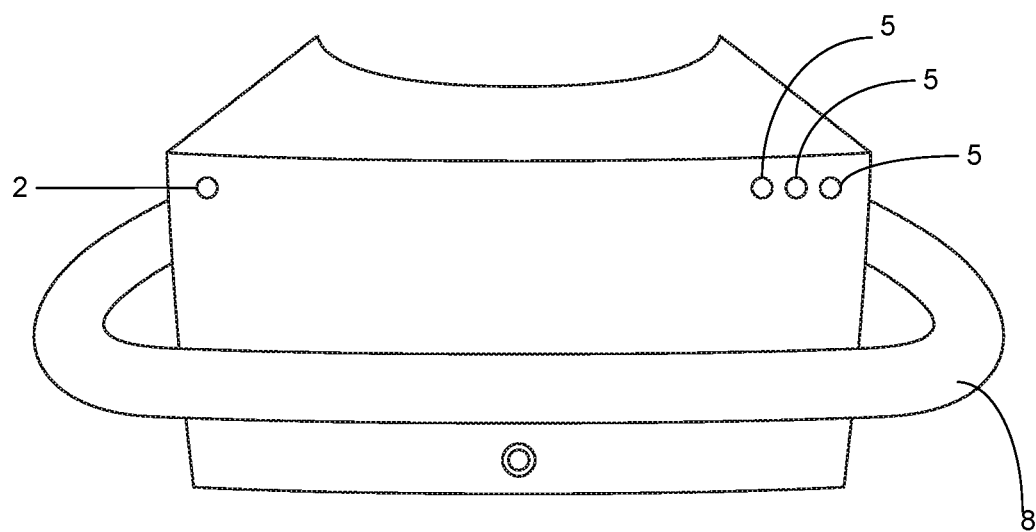
FIG. 2 is a top perspective view of the external member of the present invention.

Referring now to the drawings submitted herewith, wherein various elements depicted therein are not necessarily drawn to scale and wherein through the views and figures like elements are referenced with identical reference numerals, there is illustrated an endotracheal tube insertion apparatus 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Now referring to the drawing submitted herewith, the endotracheal tube insertion apparatus 100 includes an external member 10. The external member 10 includes housing 12 including a plurality of walls 14 that are contiguously formed to create an interior volume and the shape of the external member 10. The housing 12 is manufactured from a suitable durable material such as but not limited to plastic and includes an integrated power supply (not illustrated herein) disposed in the interior volume thereof. It should be understood within the scope of the present invention that the power supply disposed within the housing is a conventional AC or DC power supply that is configured to provide the necessary power to operate certain components of the endotracheal tube insertion apparatus 100 discussed further herein. The housing includes a bottom wall 16 that is arcuate in form being defined by perimeter edges 17, 18. The arcuate form of the bottom wall 16 is configured to as to promote a mateable engagement with a human neck during use of the endotracheal tube insertion apparatus 100. During use of the endotracheal tube insertion apparatus 100, the external member 10 is superposed the neck of a user so as to provide guidance and location detection of the insertion member 40 as is further discussed herein. The radius of the bottom wall 16 is generally equivalent to that of a human neck so as to facilitate secure placement thereon. While the bottom wall 16 is arcuate in form in a preferred embodiment, it is contemplated within the scope of the present invention that the bottom wall 16 could be formed in alternate shapes.

The housing 12 includes a handle 8 that is operably coupled thereto and is configured to facilitate carrying of the external member 10. It should be understood within the scope of the present invention that the handle 8 could be provided in alternate shapes and sizes so as to accomplish the desired objective herein. A second handle 7 is additionally provided wherein the second handle 7 is configured to have secured thereto a conventional carry strap (not illustrated herein). The external member 10 has present on the bottom surface 19 thereof a magnet 20. The magnet 20 is centrally located on the bottom surface 19 and is a conventional ferromagnetic magnet or other type of magnet. The magnet 20 is operably to magnetically attract the magnet member 45 of the insertion member 40 as is further discussed herein. It is contemplated within the scope of the present invention that the magnet 20 could be provided in alternate strengths and sizes in order to execute the desired objective discussed herein. The magnet 20 has mounted surroundably thereto a flux shield 27. The flux shield 27 is a conventional flux shield and is configured to ensure a defined area of magnetic field produced by the magnet 20. While one magnet 20 is discussed and illustrated herein, it is contemplated within the scope of the present invention that the external member 10 could have more than one magnet 20.

The external member 10 further includes a proximity sensor 30 located on the bottom surface 19. The proximity sensor 30 is operable to be communicably coupled with the proximity tag member 48 of the insertion member 40. During use of the endotracheal tube insertion apparatus 100, the proximity sensor 30 detects the presence and proper location of the end member 50 of the insertion member 40 wherein the end member 50 has formed thereon the proximity tag member 48. While one proximity tag member 48 is illustrated herein, it is contemplated within the scope of the present invention that the end member 50 could have more than one proximity tag member 48 wherein the configuration thereof could be utilized to provide incremental positioning feedback. The lights 5 present on the top wall 3 of the external member 10 provide a gradient illumination pattern that provides a visual confirmation that the proximity tag member 48, and as such the end member 50, is in the proper location during use of the endotracheal tube insertion apparatus 100 to perform an endotracheal intubation. A plurality of lights 5 are provided so as to generate an illumination pattern wherein the proper location of the end member 50 will result in illumination of all of the lights 5. Additionally, light 2 provides confirmation of communicable detection of the proximity tag member 48 and the proximity sensor 30. It should be understood within the scope of the present invention that while three lights 5 are illustrated herein, the external member 10 could be provided with more than three lights. Furthermore, it is contemplated within the scope of the present invention that various technologies could be employed for the proximity sensor 30 and proximity tag member 48 to provide the desired function but good results have been achieved utilizing radio frequency sensors. While not illustrated herein, it is additionally contemplated within the scope of the present invention that the external member 10 could be equipped with an audio alarm wherein the audio alarm could be used to provide audial confirmation of the correct location of the end member 50.

Figure 3:
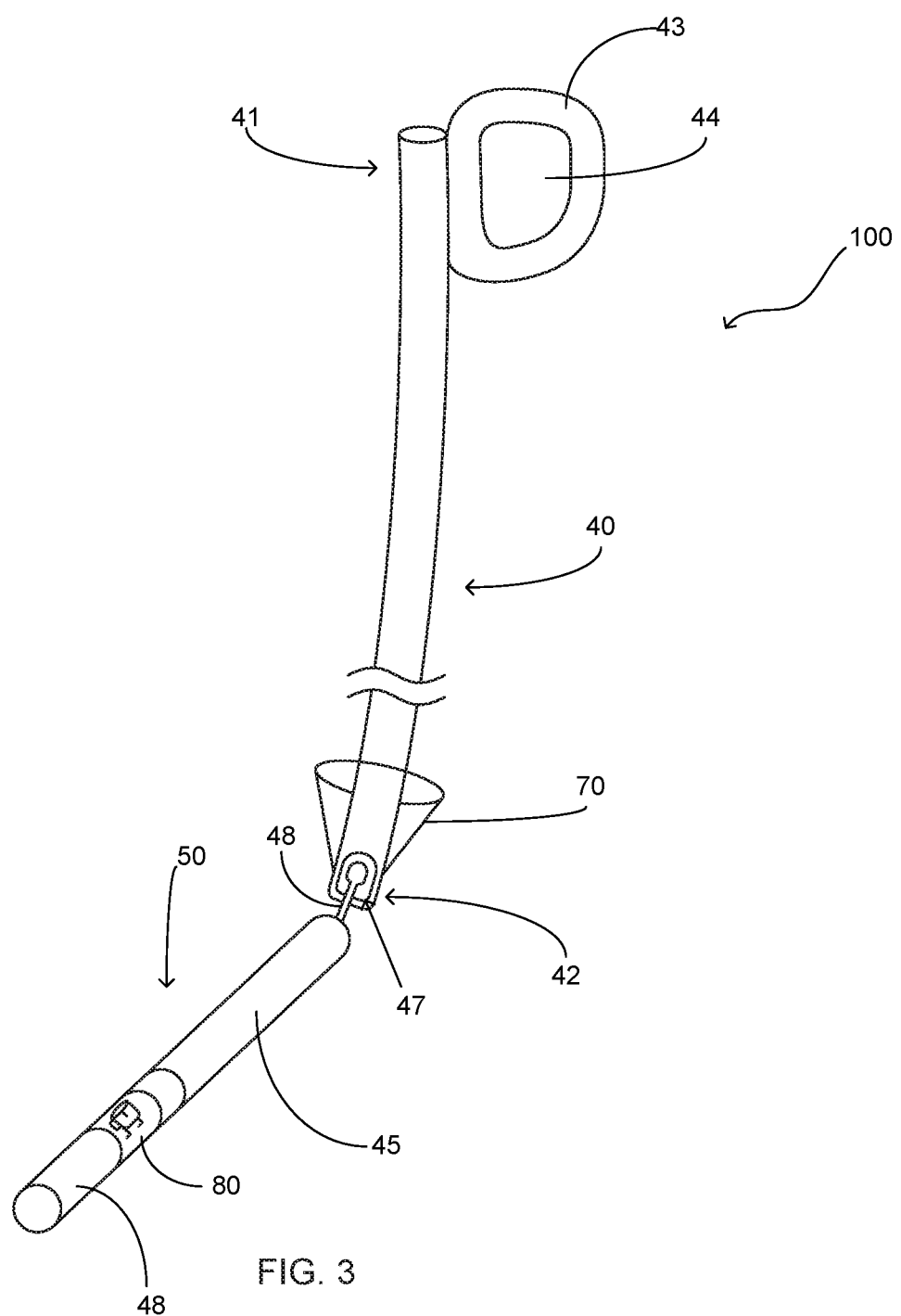
FIG. 3 is a perspective view of the insertion member of the present invention.
Figure 4:
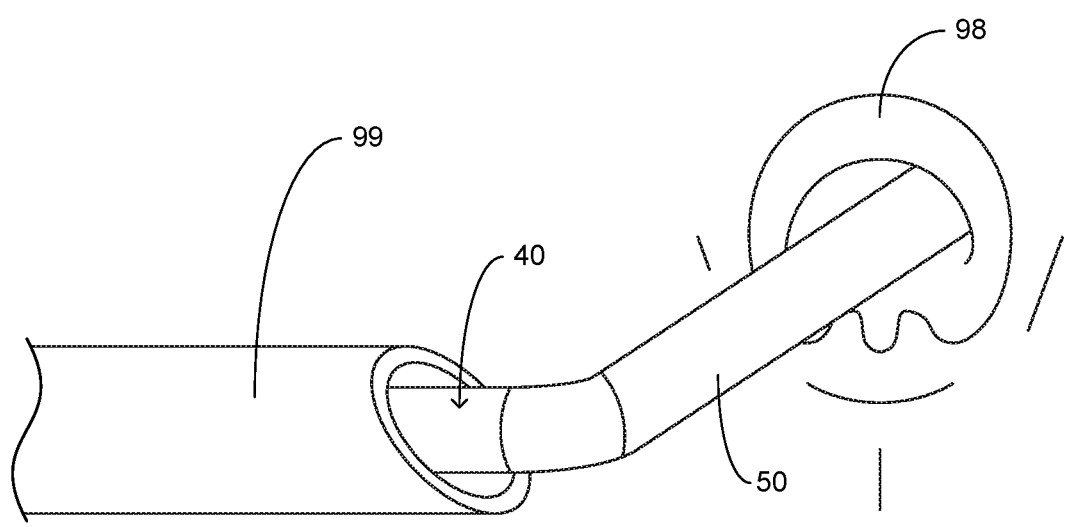
FIG. 4 is a perspective view of the insertion member operably coupled with a portion of an endotracheal tube positioned for entry through vocal cords.

Referring now to FIGS. 3 and 4 submitted as a part hereof, the insertion member 40 of the endotracheal tube insertion apparatus 100 is illustrated therein. The insertion member 40 includes a first end 41 and second end 42 and is tubular and elongated in form. The insertion member 40 is manufactured from a pliable material such as but not limited to plastic. Proximate the first end 41 is an engagement member 43 wherein the engagement member 43 is secured utilizing suitable durable techniques. The engagement member 43 in a preferred embodiment is loop shaped so as to allow a user to place at least one finger in the opening 44. While a preferred shape of the engagement member 43 is illustrated herein, it is contemplated within the scope of the present invention that the engagement member 43 could be provided in alternate sizes and shapes.

Formed on the second end 42 of the insertion member is joint member 47. Joint member 47 is designed to movably couple with member 48 so as to provide a movable coupling between the insertion member 40 and the end member 50. The movable coupling of the insertion member 40 and the end member 50 enables the required movement of the end member 50 so as to guide an endotracheal tube, in which the insertion member 40 and end member 50 are in the interior passage thereof, in the proper location and direction. During use of the endotracheal tube insertion apparatus 100, the end member 50 extends beyond the distal end of a endotracheal tube so as to provide guidance thereof utilizing the aforementioned magnet 20 and magnet member 45. The attraction of the magnet member 45 towards the magnet 20 when the external member 10 is in position on a patient's neck provides the guidance of the endotracheal tube 99 to the proper location during intubation of a patient. While a ball joint type joint is illustrated herein to movably couple the insertion member 40 and end member 50, it is contemplated within the scope of the present invention that various alternate elements could be utilized to facilitate the desired movable coupling of the insertion member 40 and end member 50. Additionally, it is contemplated within the scope of the presentation that the aforementioned movement could further be executed with materials and/or material construction of the endotracheal tube insertion apparatus 100. By way of example but not limitation, the insertion member 40 and end member 50 could be contiguously formed and manufactured of a material that may be pliable at a specific location in order to facilitate the movement of the end member 50.

The insertion member 40 further includes a guide member 70. The guide member 70 is conical in shape and is located proximate the second end 42 of the insertion member 40. The guide member 70 is manufactured from a soft pliable material such as but not limited to silicon. The guide member 70 functions to inhibit the snagging of the end of the endotracheal tube 99 on vocal cords 98 during the use of the endotracheal tube insertion apparatus 100 to perform an intubation on a patient. The guide member 70 is in a first orientation during insertion as shown herein in FIG. 3, and due to the material thereof, will invert during removal of the endotracheal tube insertion apparatus 100 so as to provide improved removal of the endotracheal tube insertion apparatus 100 from an endotracheal tube 99. It should be understood within the scope of the present invention that the guide member 70 could be provided in alternate shapes and sizes and still achieve the desired function as described herein.

The end member 50 further includes a light 80. In a preferred embodiment the light 80 is a high intensity LED light that can be seen through the patient's skin on their neck if the end member 50 is in the correct position. If the endotracheal tube insertion apparatus 100 is not in the correct position the light 80 will not be visible. It is contemplated within the scope of the present invention that the light 80 includes an integrated power source such as but not limited to a button cell battery. While not particularly illustrated herein, it is contemplated within the scope of the present invention that the insertion member 40 and/or end member 50 or any portions thereof could be covered with a sheath so as to facilitate improved utilization thereof.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding description is, therefore, not intended to be limited to the specific forms set forth herein, but on the contrary, it is intended to cover such alternatives, modifications, and equivalents, as can be reasonably included within the spirit and scope of the invention.

What is claimed is:

1. An endotracheal tube insertion apparatus that is operable to provide assistance to a user during intubation of a patient wherein the endotracheal tube insertion apparatus comprises:

an external member, said external member having a housing, said housing having a plurality of walls forming an interior volume, said external member having a bottom surface, said bottom surface being configured to be superposed the patient's neck, at least one magnet, said at least one magnet being disposed within said external member, said at least one magnet being proximate said bottom surface;

an insertion member, said insertion member being elongated in form, said insertion member having a first end and a second end, said insertion member having an engagement member proximate said first end, said insertion member being configured to be disposed within a hollow passage of an endotracheal tube;

an end member, said end member being movably coupled to said second end of said insertion member, said end member further including a magnet member, said magnet member configured to be attracted to said at least one magnet disposed in said external member; and wherein said end member propagates outward from an end of the endotracheal tube during intubation of a patient so as to guide the endotracheal tube in a desired direction for successful intubation of a patient.

2. The endotracheal tube insertion apparatus as recited in claim 1, wherein said external member further includes at least one proximity sensor.

3. The endotracheal tube insertion apparatus as recited in claim 2, wherein said end member includes at least one proximity tag member, said at least one proximity tag member being communicably coupled to said at least one proximity sensor, said at least one proximity tag member configured to provide location information concerning said end member.

4. The endotracheal tube insertion apparatus as recited in claim 3, wherein said end member further includes a light, said light being operable to provide a visual indicator of said end member.

5. The endotracheal tube insertion apparatus as recited in claim 4, wherein said insertion member further includes a guide member, said guide member being secured to said second end of said insertion member, said guide member having a first position and a second position.

6. The endotracheal tube insertion apparatus as recited in claim 5, wherein said guide member is conical in shape, said guide member in said first position positioned to inhibit the endotracheal tube from snagging on vocal cords while passing therethrough.

7. The endotracheal tube insertion apparatus as recited in claim 6, wherein in said second position said guide member is inverted so as to facilitate removal of the endotracheal tube insertion apparatus.

8. An endotracheal tube insertion apparatus configured to be operably coupled with an endotracheal tube during insertion thereof on a patient wherein the endotracheal tube insertion apparatus comprises:

an external member, said external member having a housing, said housing having a plurality of walls forming an interior volume, said external member including at least one handle formed on an exterior surface thereof, said bottom surface being configured to be superposed the patient's neck, said bottom surface further having at least one proximity sensor, said at least one proximity sensor being proximate said bottom surface;

a magnet, said magnet being disposed within said external member, said magnet being proximate said bottom surface, said magnet having a flux shield surroundably present thereto;

an insertion member, said insertion member being elongated in form, said insertion member having a first end and a second end, said insertion member being configured to be disposed within a hollow passage of an endotracheal tube;

an end member, said end member being movably coupled to said second end of said insertion member, said end member further including a magnet member, said magnet member configured to be attracted to said magnet disposed in said external member so as to guide an end of the endotracheal tube in a desired direction, wherein said end member includes at least one proximity tag member, said at least one proximity tag member being communicably coupled to said at least one proximity sensor; and wherein said end member propagates outward from the end of the endotracheal tube during intubation of a patient.

9. The endotracheal tube insertion apparatus as recited in claim 8, and further including a plurality of lights, said plurality of lights configured to provide visual confirmation of a location of said proximity tag member.

10. The endotracheal tube insertion apparatus as recited in claim 9, wherein said end member further includes a light, said light operable to be visible through skin on the patient's neck, said light operable to provide visual confirmation of a location of said end member.

11. The endotracheal tube insertion apparatus as recited in claim 10, wherein said insertion member further includes a guide member, said guide member being secured to said second end of said insertion member, said guide member having a first position and a second position.

12. The endotracheal tube insertion apparatus as recited in claim 11, wherein in said first position, said guide member is tapered over the end of the endotracheal tube being inserted into a patient.

13. The endotracheal tube insertion apparatus as recited in claim 12, wherein said external member further includes an audio alarm, said audio alarm operable to provide audial confirmation of a location of the end member.

14. The endotracheal tube insertion apparatus as recited in claim 13, wherein in said second position said guide member is inverted so as to so as to facilitate removal of the endotracheal tube insertion apparatus from an endotracheal tube.

15. An endotracheal tube insertion apparatus configured to be operably coupled with an endotracheal tube so as to facilitate proper insertion of the endotracheal tube on a patient wherein the endotracheal tube insertion apparatus comprises:

an external member, said external member having a housing, said housing having a plurality of walls forming an interior volume, said external member including at least one handle formed on an exterior surface thereof, said external member having a bottom surface that is arcuate in shape, said bottom surface being configured to be superposed the patient's neck, said bottom surface further having at least one proximity sensor, said at least one proximity sensor being proximate said bottom surface;

a magnet, said magnet being disposed within said external member, said magnet being proximate said bottom surface, said magnet having a flux shield surroundably present thereto;

an insertion member, said insertion member being elongated in form, said insertion member having a first end and a second end, said insertion member being configured to be disposed within a hollow passage of an endotracheal tube, said insertion member having a coupling, said coupling being at said second end of said insertion member;

an end member, said end member having a first end and a second end, said end member having a coupling at said first end of said end member, said coupling of said first end of said end member configured to operably couple with said coupling of said insertion member located at said second end of said insertion member so as to provide a movable connection between said insertion member and said end member, said end member further including a magnet member, said magnet member configured to be attracted to said magnet disposed in said external member so as to guide an end of the endotracheal tube in a desired direction, said end member further including at least one proximity tag member, said at least one proximity tag member being communicably coupled to said at least one proximity sensor;

a light, said light being located on said end member, said light providing a visual indication of proper location of the endotracheal tube; and wherein said second end of said end member propagates outward from the end of the endotracheal tube during intubation of a patient.

16. The endotracheal tube insertion apparatus as recited in claim 15, wherein said external member includes a plurality of lights, said plurality of lights configured to illuminate in a progression during proper location of the end member during intubation of the patient.

17. The endotracheal tube insertion apparatus as recited in claim 16, wherein said insertion member further includes a guide member, said guide member being secured to said second end of said insertion member, said guide member being conical in shape, said guide member being manufactured from a pliable material, said guide member having a first position and a second position.

18. The endotracheal tube insertion apparatus as recited in claim 17, wherein said guide member is configured to inhibit snagging of an end of the endotracheal tube during intubation.

19. The endotracheal tube insertion apparatus as recited in claim 18, and further including an audio alarm, said audio alarm operable to provide confirmation of proper location of said end member.

20. The endotracheal tube insertion apparatus as recited in claim 19, wherein said proximity sensor and said proximity tag member are RFID.

* * * * *